United States Patent [19]

Beacham

[11] 4,361,279

[45] Nov. 30, 1982

[54] COMBINED CONTAINER AND DISPENSER FOR VOLATILE PRODUCT

[75] Inventor: Robert C. Beacham, Pleasanton, Calif.

[73] Assignee: The Clorox Company, Oakland, Calif.

[21] Appl. No.: 203,189

[22] Filed: Nov. 3, 1980

[51] Int. Cl.³ .............................................. A61L 9/00
[52] U.S. Cl. .................................... 239/56; 239/58
[58] Field of Search ................. 239/56, 58, 55, 57, 239/54, 53, 59, 60, 34, 36; 220/306, 315, 323, 23.4

[56] References Cited

U.S. PATENT DOCUMENTS

| | | | |
|---|---|---|---|
| 2,959,354 | 11/1980 | Beck | 239/53 |
| 3,964,684 | 6/1976 | Schimanski | 239/56 |
| 4,004,734 | 1/1977 | Hadtke | 239/58 |

*Primary Examiner*—James B. Marbert
*Attorney, Agent, or Firm*—Stephen M. Westbrook

[57] ABSTRACT

A combined container and dispenser for dispensing a volatile product such as air freshener or insecticide by volatilization of the product from within the container includes an annular cup having a threaded axial hub and a peripheral flange defining a seal surface. A spheroidal cap has a threaded axial stem arranged for progressive threaded coupling with the hub and an annular seal ring disposed at the outer edge of the cap and arranged to sealingly engage the seal surface of the cup to form a sealed container therewith. A cellulose pad impregnated with a volatile product is disposed on ribs provided on the hub in interference relationship therewith and has its outer edge supported by vane-like support members on the outer portion of the cup. A flange is provided on the distal end of the stem within a counterbore formed in the bottom of the cup and hub to limit the extent to which the container may be opened by unscrewing of the cap from the cup.

The flange may be provided by heat forming, spin welding or insertion of a flanged plug into the stem.

13 Claims, 9 Drawing Figures

FIGURE 8
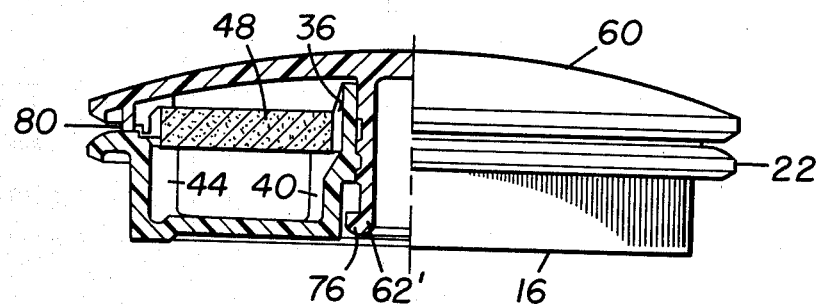
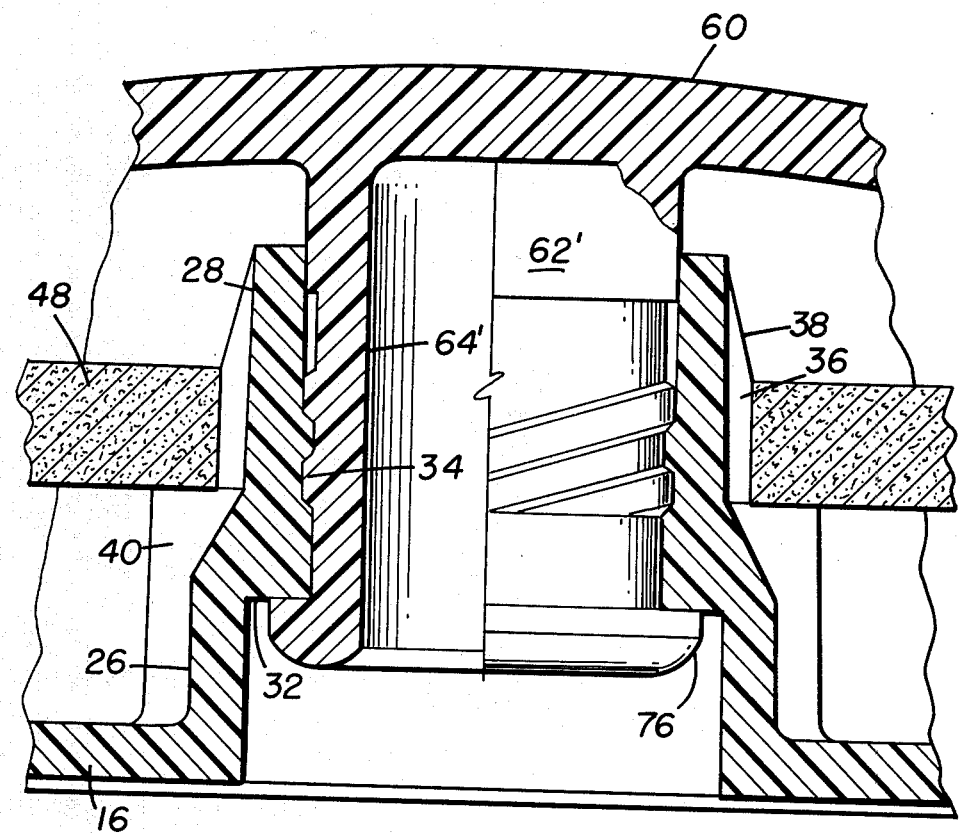
FIGURE 9

COMBINED CONTAINER AND DISPENSER FOR VOLATILE PRODUCT

BACKGROUND OF THE INVENTION

Although volatile products such as room deodorants and insecticides are often dispensed in sudden large quantities to remedy significant problems, it is also desirable to provide for continuous dispensing of such products at a low rate to provide a low residual level of product in the ambient atmosphere to prevent such problems from arising. One means of providing continuous dispensing of such products is to impregnate the product into an absorbent pad disposed within a container which may be opened a selected amount to allow a low rate of volatilization of the product to ambient atmosphere. Such containers are designed to be unobtrusively stuck, hung or otherwise attached to a hidden surface or fixture so that they are not normally observable by persons nearby. It is therefore desirable that such containers include means for attaching or affixing them to secreted surfaces which are not otherwise prepared for receiving such containers.

Such containers should also allow for controlled opening thereof for carefully regulated rates of volatilization of the product which is great enough to ensure effectiveness, but low enough to maximize the life of the unit.

In addition, it is desirable that such containers achieve an effective seal to ensure that it will exhibit extended shelf life and home storage life prior to use without significant loss of the volatile product.

Prior art devices have included adhesive surfaces and apertured tags for affixing the containers to hidden surfaces. However, they have comprised cooperating members joined at their peripheral edges to form a sealed closure, and separable to expose apertured side walls for flow of air to the volatile product contained within. The operational side walls occlude and interface with the flow of air into the interior of the container.

The cooperating members are joined at their periphery adjacent sealing lips which are easily misaligned. Such construction requires close tolerances of the coupling portions of the container to insure alignment of the seal members, since there is no means provided for self adjustment of the planar alignment of the seal elements. Furthermore, there is no means provided for compressing the sealing elements together to enhance sealing.

Such containers may also be easily, and sometimes inadvertently, fully opened by complete separation of their respective members, exposing the manipulator to direct contact with the volatile product contained within the container. This is a particular hazard when such containers are disposed under furniture or on other low surfaces where they can be easily reached by children.

Accordingly, it is an object of the present invention to provide a dispensing container for volatile products which includes means for closely controlling the degree of opening of the container to an extent chosen to ensure effectiveness while maximizing product life.

It is also an object of the present invention to provide a dispensing container that will provide assured sealing of the container whenever it is closed, through self-aligning of the sealing members of the container when the container is closed.

A further object of this invention is to provide such a container that will afford unimpeded flow of air into the interior of the container.

Another object of the present invention is to provide such a dispensing container for a volatile product which includes a torque advantage enabling the user to manually exert compressive forces on the sealing elements of the container.

A further object of the invention is to provide a container which cannot be opened beyond a preselected maximum limit which ensures that no direct contact with the volatile product contained within the container is possible.

Still another object of the present invention is to provide a dispensing container for a volatile product which will be small, and inexpensive to manufacture, but ensure complete volatilization and dispensing of the product from within the container by allowing circulation of air over all surfaces of an impregnated pad within the container.

BRIEF DESCRIPTION OF THE INVENTION

The present invention provides a container for containing and dispensing a volatile product; or for affording air access to a malodor absorbent disposed within the container. The container includes an annular cup having a threaded axial hub and a peripheral flange defining a sealing surface; and a spheroidal cap having a threaded axial stem disposed within the hub. An annular seal ring depends from the outer edge of the cap for sealing engagement with the seal surface on the cup when the stem is screwed down into the hub. The single axial attachment of the cap to the cup allows the cap to pivot a small amount within the hub for planar alignment of the seal ring with the sealing surface as the cap is screwed into the hub. In addition, the cap is constructed of plastic, and the flexibility of the plastic and spheroidal configuration of the cap allows flexing of the cap as the seal ring engages the seal surface. There is a torque advantage achieved by manual rotation of the threaded center stem by manual forces on the edge of the container. Thus, continued advancing of the cap stem into the hub will provide some flexing of the cap edge to further ensure sealing of the ring against the seal surface around the periphery of the container, as well as some compressing of the seal ring against the seal surface.

A flange is disposed on the bottom of the cap stem within a counterbore provided in the bottom of the cup hub. To open the container, the cap is unscrewed from the cup until the flange engages the bottom of the hub counterbore, at which point the seal ring will be withdrawn from the seal surface a preselected distance to provide optimum performance of the container dispenser. The hub and stem threads are limited to allow mutual slipping when the flange contacts the hub counterbore, to prevent distortion of the flange by continual manual twisting of the cap due to the torque advantage of the cap.

A cellulose pad impregnated with the volatile product to be dispensed, such as air freshener fragrance oils, is disposed on ribs provided on the hub in interference relationship therewith. The outer edge of the disk-like pad is supported on vane-like supports disposed at the outer portion of the cup. When the container is in the open configuration, it will present an annular opening, defined by the separated seal ring and seal surface, to the ambient air so that it may flow to and from the interior of the container unimpeded by operational side walls or the like.

The pad is so disposed just inward of the seal surface and the side of the cup so that air flowing over the seal surface when the seal ring is withdrawn therefrom will communicate to both the upper and lower surface of the pad. Some clearance may also be provided between the inner edge of the pad and the hub for communication of air between the cup and cap of the hub.

An apertured tag, having an adhesive surface, is provided on the bottom of the cup for affixing the container to a surface or hook as desired.

Thus, the container of the present invention provides a self-aligning device which may be securely sealed for extended storage without dissipation of volatile product disposed within, yet easily and controllably opened by manual rotation of the cap with respect to the cup to unscrew the cap until the flange engages the counterbore of the hub, preventing further opening of the container. At this configuration, the seal ring will be withdrawn from the sealing surface a preselected distance, preferably about 0.110 inches, to provide an annular passageway for communication of ambient air with the pad disposed within the container. Such insured limited opening of the container avoids any possibility of direct contact with the volatile product. The vane-like member suspension of the impregnated pad within the container minimizes the possibility of "wicking" and in flow of the active material in the pad out of the pad and container.

If desired, the container may be easily reclosed and sealed by again rotating the cap into the cup.

Thus, the container of the present invention meets the object outlined above and represents a significant advance over the state of the art.

Other objects and advantages of the invention will become apparent by review of the following specifications and claims, as well as the accompanying drawings.

DESCRIPTION OF THE DRAWINGS

In the drawings:

FIG. 8 is an elevation of an alternative embodiment of the present invention, partially in section; and FIG. 9 is an enlarged fragmentary section of the embodiment shown in FIG. 8.

BEST MODE OF PRACTICING THE INVENTION

Figure 1:
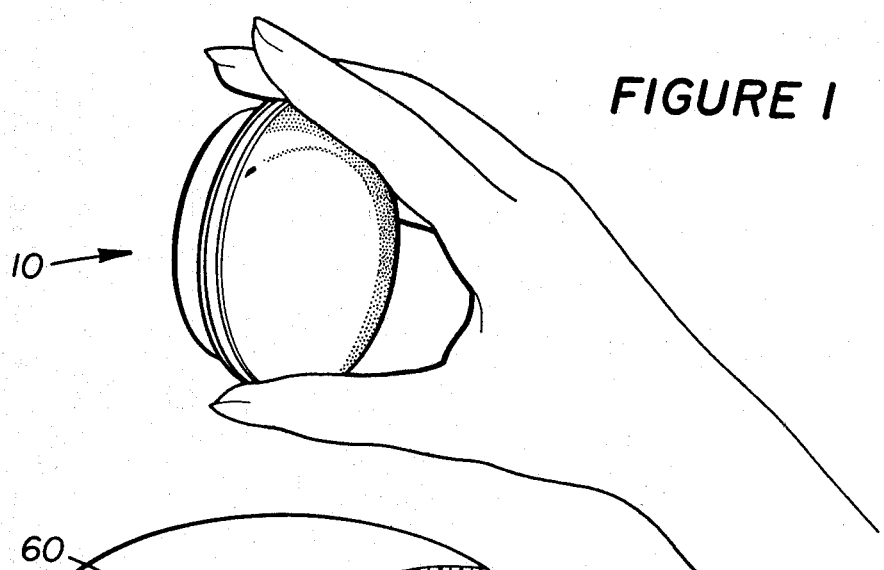
FIG. 1 is a perspective view of the container of the present invention.
Figure 2:
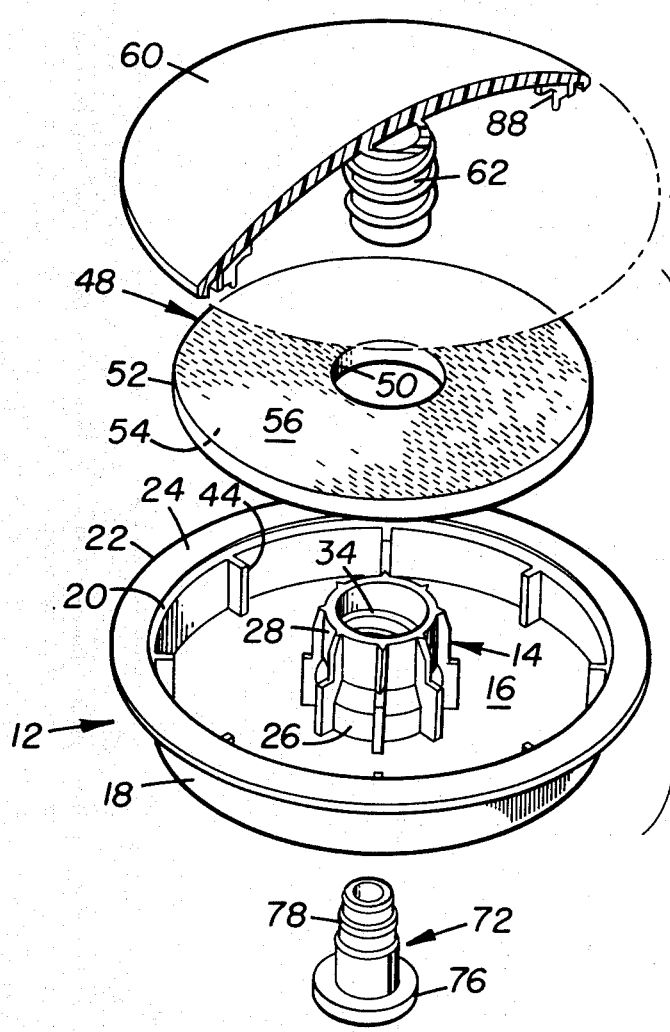
FIG. 2 is an expanded view of the container shown in FIG. 1.

Referring to the drawings, the best mode of practicing the present invention is depicted, as described hereinbelow. FIG. 1 shows a container 10 embodying the present invention as it would be manually handled for sticking or attaching to a surface or hangar. As shown in FIG. 2, the container includes a cup 12, which comprises an axial hub 14 disposed on an annular bottom 16. An annular side wall 18 is upstanding on the outer perimeter of the bottom and terminates in a top edge 20. A flange 22 is provided on the top edge of the side wall, and includes a top surface 24 which defines a sealing surface, as discussed below.

Figure 4:
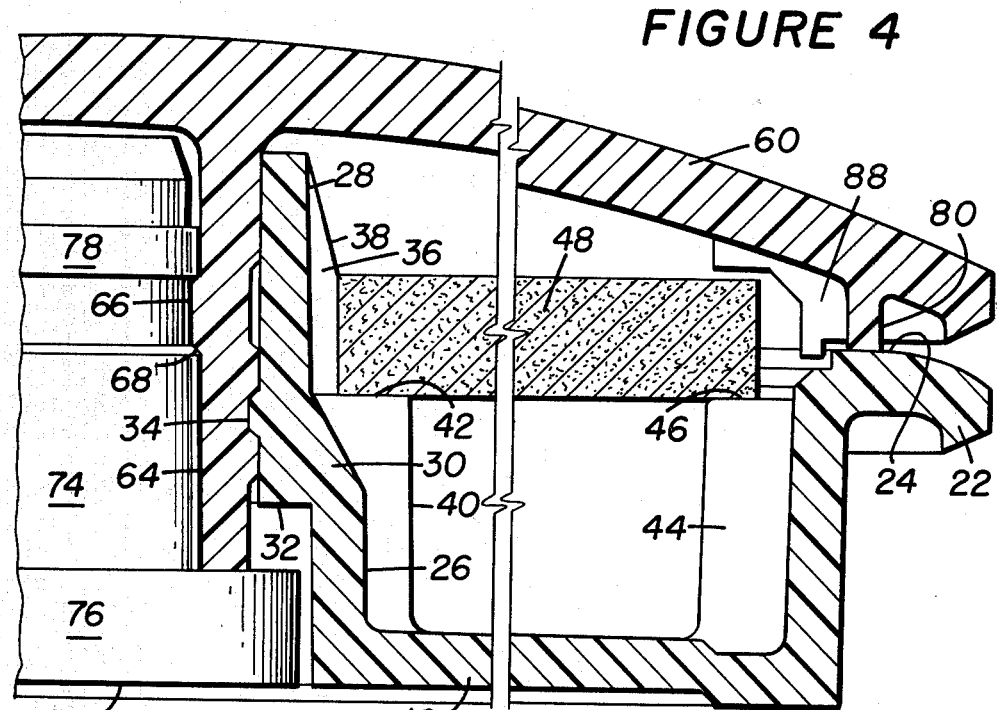
FIG. 4 is an enlarged cross-section of the container shown in FIG. 3.

Hub 14 includes a lower, larger diameter portion 26 disposed on bottom 16, and a distal, smaller diameter portion 28 joined to the lower portion at a juncture 30. Referring to FIG. 4, the internal diameter of the hub is similarly larger in the lower portion 26 and smaller within the upper portion 28; the juncture of said inner diameters forming a limit surface 32. A thread 34 is provided on the inner diameter of the upper portion of the hub. The thread is preferably a single turn thread to allow withdrawal of the cup from cooperating mold cavities during manufacture.

Referring again to FIG. 2, a plurality of radial ribs 36 are provided on the upper portion of the hub for retention of a flexible pad thereon. Ramps 38 are formed on the upper ends of the ribs for advancing of a pad onto the ribs. Stops 40 are provided at lower ends of the ribs and include surfaces 42 arranged to abuttingly engage a pad as will be described hereinbelow.

Figure 3:
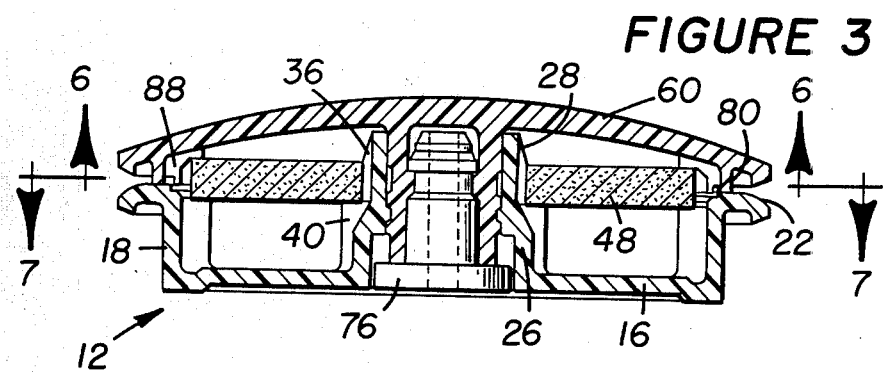
FIG. 3 is a cross-section of the container of the present invention, in the closed mode.
Figure 5:
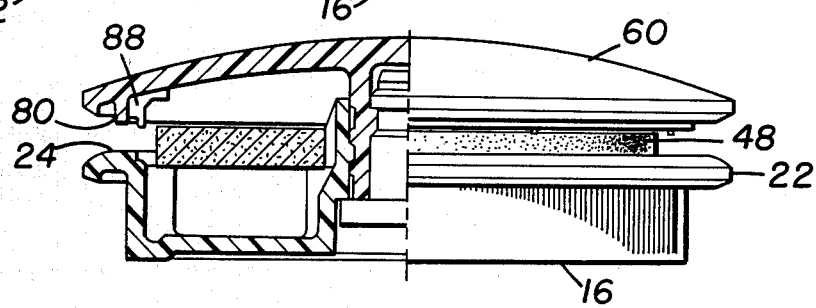
FIG. 5 is a cross-section of the container in an open mode.
Figure 6:
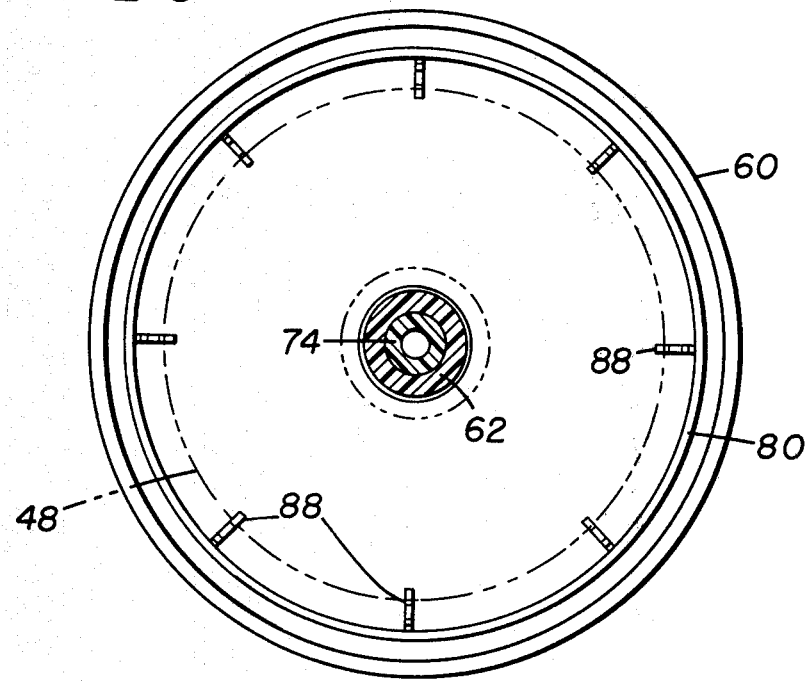
FIG. 6 is a cross-section of the container taken along the line 6—6 in FIG. 3.
Figure 7:
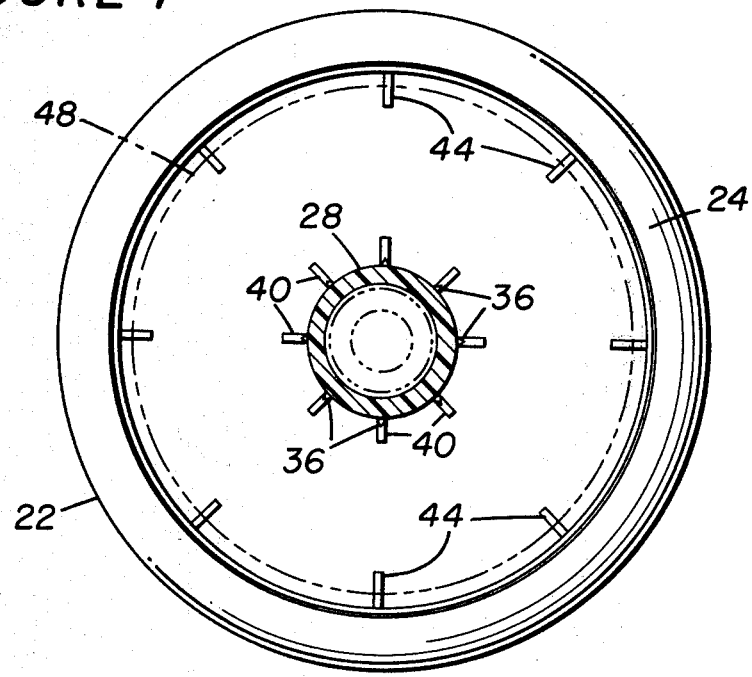
FIG. 7 is a cross-section of the container taken along the line 7—7 in FIG. 3.

Supports 44 are provided on side wall 18 and include support surfaces 46 which are coplanar with stop surfaces 42 and are also arranged to abuttingly engage a pad. As seen in FIGS. 3–5, stop surfaces 42 and support surfaces 46 are disposed slightly below the top edge of side wall 18. A disk-like pad 48 has an inner diameter 50 and an outer diameter 52; and planar lower and upper surfaces 54 and 56. The pad is constructed of an absorbent, flexible material such as cellulose, and impregnated with a volatile material to be dispensed, such as fragrance oils or insecticide. The inner diameter of the pad is disposed on ribs 36 in interference fit therewith. Ramps 38 guide the pad onto the ribs and allow the ribs to crush a small adjacent portion of the pad as the pad is urged down onto the ribs and against stop 40 and supports 44, for secure retention of the pad by the ribs. The stops and supports, and the pad thickness, are so arranged that the bottom surface of the pad is below the sealing surface 24, and the top surface of the pad is above it, so that air flowing over the sealing surface will communicate with both the top and bottom surface of the pad.

The container also includes a spheroidal cap 60, which has a hollow axial coupling comprising a threaded stem 62 which is threadably disposed in hub 14. The thread tolerances and the central axis coupling comprise means for providing limited axial rocking or pivoting of the cap with respect to the cup, allowing pivoting or rocking of the plane of a seal ring disposed on the cap, as discussed below, with respect to the seal surface on the cup, allowing planar alignment thereof.

Referring to FIGS. 3 and 4, in the closed configuration, stem 62 will project below limit surface 32 and into the enlarged inner diameter portion of the hub. Stem 62 has an internal diameter 64 which includes a reduced diameter lock ring 66 provided thereon having a ramp surface 68 on its lower edge, and a step surface 70 on its upper edge. A plug 72 adopted for locking engagement with the stem includes a shaft 74 disposed within stem 62, and a flange 76 which extends radially outwardly within the lower portion of the hub. A snap ring 78 disposed on the shaft is adapted to slide past lock ring 66 upon insertion of the plug shaft into the stem by parallel flexing of the members, and lock against step surface 70 to prevent withdrawal of the plug from the stem.

An alternative means of providing flange 76 is shown in FIGS. 8 and 9, which show a flange 76' which is formed on the lower end of stem 62' as by spin forming or ultrasonic peening after the stem is disposed in the hub.

The outer edge of the cap terminates adjacent flange 22. A seal ring 80 disposed near the outer edge depends from the cap and engages sealing surface 24 in sealing relationship therewith when stem 62 is fully inserted into hub 14, as shown in FIGS. 3 and 4. As previously discussed, the cap stem rocks or pivots in the threaded hub to accommodate alignment of the plane of seal ring 80 with seal surface 24, to enhance sealing. In addition, a torque advantage is afforded by further rotation of the axial stem by exertion of manual forces on the edge of the cap which provides some flexing of the cap to further insure firm contact of the seal ring with the seal surface around the perimeter of the cap and cup. Such torque advantage will also provide for some compression of the seal ring against the seal surface for even more effective sealing of the cap and cup.

Therefore, in this mode the cup and cap provide a sealed container for the pad, preventing any communication of outside air with the pad. Thus, the pad and container may be transported and stored for extended periods without affecting the life of the product when it is ready to use.

When the product is to be used, the cap and cup are rotated mutually counter-clockwise, withdrawing stem 62 from hub 14 a preselected distance until flange 76 engages limit surface 32, as shown in FIGS. 5 and 9. The threads on stem 62 and hub 14 are so arranged that their ends will just meet and slip past each other when the flange engages the limit surface, which prevents the torque advantage achieved in the cap from over distorting or destroying the flange. During said rotation, seal ring 80 will be correspondingly withdrawn from sealing surface 24, providing a passageway 82 for communication of outside air to the pad. When the cap is raised from the cup, there will be an annular opening defined by the separated seal ring and seal surface, which will allow unimpeded flow of ambient air to and from the interior of the container.

The outer diameter of the pad is less than the inner diameter of the cup, leaving an annular passage 84 therebetween which allows air to circulate between the recessed area of the cup below the pad and the outside of the container. Clearance is also provided between the pad and the cap, allowing communication of outside air with the top of the pad and the interior of the cap.

The inner diameter of the pad, disposed on the ribs, is greater than the lesser diameter of the hub, providing a space between the hub and the inner diameter of the pad for some circulation of air between the cap and cup at the hub. The pad is completely supported on the ribs, stops and supports, which are all vane-like in construction and present minimum surface contact to the pad. Accordingly, the opportunity for the ingredient impregnating the pad to "wick" and flow out of the pad onto the container surface is minimized.

A plurality of pins 86 are provided on legs 88 and arranged to depend below seal ring 80 inwardly adjacent the seal ring and flange 22, above the top edge of the side wall. The pins serve as bearing surfaces for the bottom of the cap prior to assembly to avoid damage to the seal ring.

A dress ring 90, which extends below the bottom of the cup, is provided on the outer edge of the bottom of the cups to provide a bearing surface for the cup. The recessed bottom may thus be provided with a label or tag that will not be abraded by sliding of the container on its bottom.

An adhesive tag may be provided on bottom 16 to provide means for sticking or hanging the container on a support surface.

The label disposed on the bottom surface may include an apertured tag for hanging the container on a hook, wire or nail.

The present invention thus provides a dispensing container for a volatile product that can be inexpensively constructed by plastic molding and easily assembled to a self-aligned and sealed container. Such sealing ensures a longer shelf life for the product.

When ready for use, the container is easily manipulated to a predetermined optimum configuration by unscrewing of the cap to the extent allowed, opening the cap from the cup a desired amount (preferably 0.110 inches) to allow an effective but economical rate of dispersion of the volatile ingredient.

The container cannot be opened by the consumer more than the aforesaid predetermined amount, ensuring that the consumer, or curious children, will not be inadvertently exposed to direct contact with the active invention can be obtained from a study of the drawings, the disclosure and the appended claims.

What is claimed is:

1. A container for a volatile product comprising; an annular cup including first axial coupling means for coupling of a closure to the cup, an annular recess disposed around the coupling means, and a rim disposed on the perimeter of said annular recess, said rim including means defining a seal surface thereon which is normal to said axial coupling,
   a closure comprising a cap having a second axial coupling means adapted for coupling with said first axial coupling means,
   said coupling means being threadably engagable for coupling of said cap to said cup in selective engagement therewith as said cap is rotated with respect to said cup, said cap and said cup being manually engagable on rims spaced radially from said coupling means for torque advantage in engaging said cap and said cup,
   an annular seal ring disposed on the cap and arranged to contact said seal surface when said coupling means are fully engaged, and wherein said seal ring will form with said seal surface an axial compression seal upon tightening of the cap against the cup.

2. The container defined in claim 1 wherein said first axial member comprises a hub having axial ribs, and further comprising an annular absorbent pad disposed on said ribs in interference fit therewith.

3. The container defined in claim 2 further comprising stop means provided on said hub for positioning said pad when in abutment therewith in registration with said seal surface, and support means provided on the perimeter of said annular recess for supporting the perimeter of the absorbent pad adjacent to said seal surface whereby the pad will be disposed inwardly adjacent an annular aperture defined by said seal surface and seal ring when the cap is selectively disengaged from the cup.

4. The container of claim 1 wherein said coupling means include means for providing axial pivoting of the cap with regard to the cup for planar alignment of the seal ring and seal surface.

5. The container defined in claim 1 wherein said cap is constructed of flexible plastic whereby upon progressive engagement of said threaded coupling means said cap will flex to allow compressive seating of the seal ring on the seal surface.

6. The container defined in claim 5 wherein said cap is spheroidal.

7. The container defined in claim 2 wherein said ribs include ramps for advancing the pad onto the ribs into interference fit relationship therewith.

8. The container of claim 1 wherein said cup further comprises a limit surface provided on the cup and limit means for limiting disengagement of the threaded couplings, said limit means including flange means provided on the distal end of the second coupling means and arranged to engage said limit surface upon preselected disengagement of said threaded coupling means.

9. The container defined in claim 8 wherein said limit means comprises a flange provided on the end of the second coupling means.

10. The container defined in claim 8 wherein said second coupling means has an open end, and said limit means comprises a plug disposed in said open end having a flange provided thereon.

11. The container defined in claim 8 wherein said limit means further comprises means for limiting the thread engagement of the threaded couplings when the flange means engages the limit surface.

12. The container of claim 11 wherein said hub has a smaller diameter at its distal end, and a larger diameter at a lower end secured to said cup bottom, defining a counterbore in said bottom providing said limit surface at the inner juncture of the smaller and larger inner diameters of the hub.

13. A container for retaining and dispensing an air freshener or the like comprising a hub having external axial ribs, and an internal thread, an annular absorbent pad disposed on said hub in interference fit with said ribs, an annular rim defining a seal surface disposed outwardly adjacent of said absorbent pad, a recessed cup portion connecting said rim to said hub on one side of said absorbent pad and spaced from said pad, a cap disposed on and spaced from the other side of said pad, said cap including a threaded stem coupled to said hub, and an annular seal ring disposed in juxtaposition from said seal surface, whereby upon selective rotation of the cap with respect to the hub the seal ring will compressively engage the seal surface for closure of the container, or be spaced from said surface for opening thereof.

* * * * *